United States Patent [19]

Kurtz et al.

[11] 4,424,053

[45] Jan. 3, 1984

[54] DISPOSABLE AUTOTRANSFUSION DEVICE

[75] Inventors: Leonard D. Kurtz, Woodmere; Joseph LiCausi, Port Jefferson Station, both of N.Y.

[73] Assignee: BioResearch Inc., Farmingdale, N.Y.

[21] Appl. No.: 290,666

[22] Filed: Aug. 5, 1981

[51] Int. Cl.³ .......................................... A61M 35/00
[52] U.S. Cl. ....................................................... 604/4
[58] Field of Search ............ 128/214 B, 214 E, 214 F, 128/276–278, 297; 417/328; 222/207, 335; 141/67, 258; 137/205; 604/4, 7, 30, 31, 35, 37, 38, 134, 135, 140, 141, 149, 151, 152, 210, 412

[56] References Cited

U.S. PATENT DOCUMENTS

| | | | |
|---|---|---|---|
| 2,828,694 | 4/1958 | Nallinger | 417/328 |
| 3,162,324 | 12/1964 | Houser | 222/207 |
| 3,799,702 | 3/1974 | Weischaar | 128/278 X |
| 3,965,896 | 6/1976 | Swank | 604/4 |
| 4,231,366 | 11/1980 | Schael | 128/214 E |
| 4,261,362 | 4/1981 | Kurtz et al. | 128/276 |
| 4,278,089 | 7/1981 | Huck et al. | 128/278 |

Primary Examiner—C. Fred Rosenbaum
Assistant Examiner—J. L. Kruter
Attorney, Agent, or Firm—Larson and Taylor

[57] ABSTRACT

An autotransfusion device for collecting blood from a pool in a patient and for subsequently returning the collected blood to the circulatory system of the patient is disclosed. The device includes a liquid collection chamber having a movable wall and a stationary wall. The liquid collection chamber is connected to the pool of blood by an aspirator and to a suction source to draw the blood into the collection chamber. After the collection chamber is filled to the capacity desired, a compressed spring is released to urge the movable wall toward the stationary wall. The blood is forced out of the collection chamber by the compressed spring and back to the circulatory system of the patient.

11 Claims, 2 Drawing Figures

DISPOSABLE AUTOTRANSFUSION DEVICE

FIELD OF THE INVENTION

This invention relates generally to an autotransfusion device and more particularly to a disposable autotransfusion device having a collection chamber and a member for forcing blood from the collection chamber.

BACKGROUND OF THE INVENTION

During certain types of surgery, especially during chest cavity surgery, the patient frequently loses large amounts of blood. Ordinarily, the lost blood is aspirated away and the patient is given a transfusion of donated blood to make up for the blood which is lost. While this system has proven to be satisfactory, there are a number of problems associated with donated blood.

In order to reduce the problems associated with donated blood, it has been proposed in the prior art to collect the blood lost from the patient and return this blood to the circulatory system of the patient. For example, in U.S. Pat. No. 3,191,600 (Everett), an autotransfusion apparatus is disclosed which includes a vacuum source and a plurality of suction tips for immersion in pools of blood. The blood is collected in a collection chamber and is returned to the patient through a one-way valve. Another autotransfusion device is disclosed in U.S. Pat. No. 3,492,991 (Dyer, Jr.) and includes a container equipped with a filter through which the blood is gravity fed back to the patient. In U.S. Pat. No. 3,993,067 (Schachet et al.), an autotransfusion device is disclosed in which the blood is forced back to the patient by pressure in the collection chamber. Still another autotransfusion device is disclosed in U.S. Pat. No. 4,047,526 (Reynolds et al.). This patent discloses a collection chamber in which blood is continuously aspirated. A blood bag with an outwardly urged spring is connected to the collection chamber to withdraw some of the blood therefrom. The blood collected in the blood bag is then later reintroduced into the patient.

There has also been disclosed in the prior art a spring operated device which forces blood from a blood bag into the patient. Such a device is disclosed in U.S. Pat. No. 3,565,292 (Jinotti).

While autotransfusion has been disclosed in the prior art, these devices have tended to be complicated and unwieldy. In addition, the devices have been relatively expensive and required careful upkeep.

SUMMARY OF THE INVENTION

In accordance with the present invention, a disposable autotransfusion device is provided with a collection chamber having a stationary wall and a movable wall. The collection chamber is connected to a suitable source of vacuum by a suction hose and to the pool of blood through the aspirator hose and into the collection chamber. The collection chamber or blood bag is formed of flexible material so that the side walls move inwardly when suction is applied. However, the length to cross section ratio of the blood bag is such that the side walls cannot seal together to form an hour glass configuration with upper and lower chambers sealed off from each other. Thus, with the present invention, blood entering the bag will pass to the bottom of the bag. After the collection chamber is filled to the extent desired, the hoses to the source of vacuum and pool of blood are closed off and a spring is released from its locked position to urge the movable wall toward the stationary wall. Initially, all of the air which remains in the collection chamber is allowed to bleed from the collection chamber as the movable wall moves. After this air is removed, the collection chamber is connected to the circulatory system of the patient and the spring forces the blood in the collection chamber back into the patient.

According to a preferred embodiment, the collection chamber is formed by a blood bag which is located between the stationary wall and the movable wall. In addition, the suction source is connected to the movable wall which is at the top of the collection chamber. The outlet of the suction source in the collection chamber has an inverted cone-shaped portion to facilitate air removal and to help prevent liquids from being drawn to the suction source. Located above the inverted cone-shaped portion is a float valve to prevent liquids from entering the suction source and to assist in the removal of air from the collection chamber to eliminate the air-liquid interface. A locking device is also provided to hold the movable wall against the force of the spring until the collection chamber is filled to the extent desired.

With the present invention, a relatively simple, inexpensive and reliable autotransfusion device is provided. The autotransfusion device is provided in a sterile package so that it can be quickly and easily connected to a source of vacuum and to the patient. When the collection chamber is filled, a new sterile autotransfusion device is similarly, quickly, and easily substituted for the filled device. The self-contained spring in the filled device is then released causing the collected blood to be forced back into the patient efficiently and effortlessly. An adjustable clamp on the return hose controls the flow of blood back to the patient. After the collected blood has been returned to the patient, the inexpensive device is thrown away.

Other features and advantages of the present invention are stated in or apparent from the detailed description of a presently preferred embodiment of the invention found hereinbelow.

DETAILED DESCRIPTION OF THE PREFERRED EMBODIMENT

Figure 2:
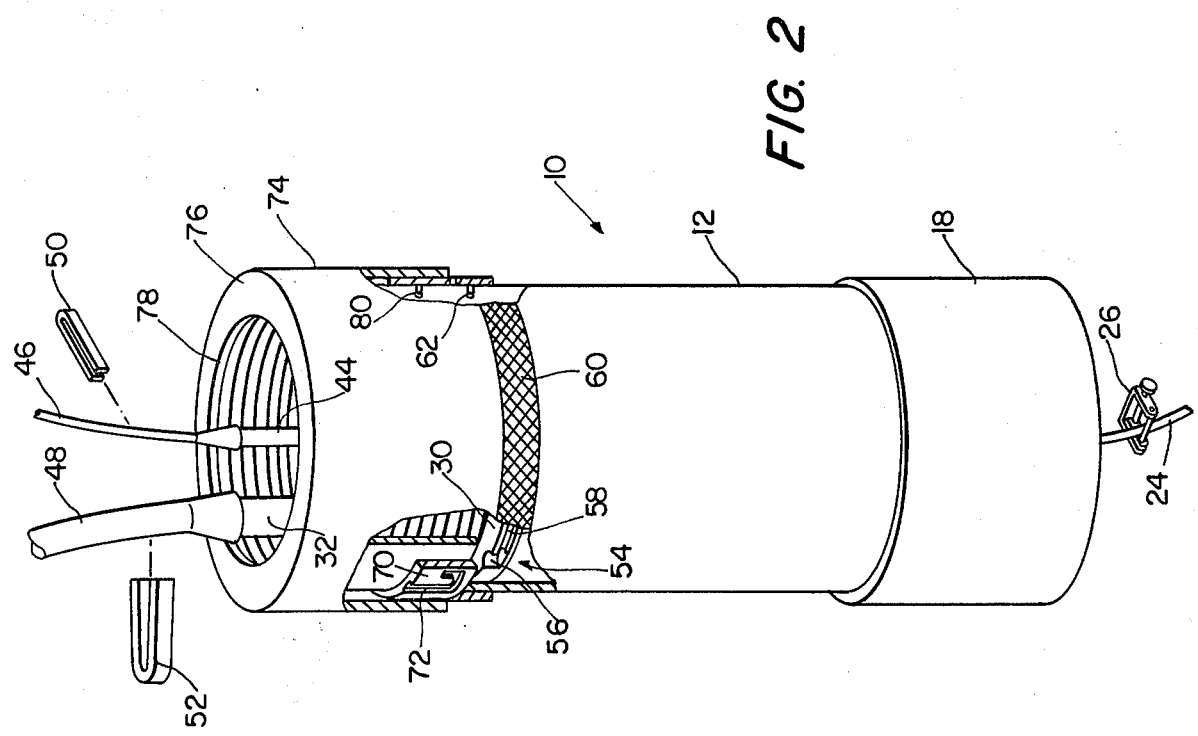
FIG. 2 is a perspective view of the autotransfusion device depicted in FIG. 1.
Figure 1:
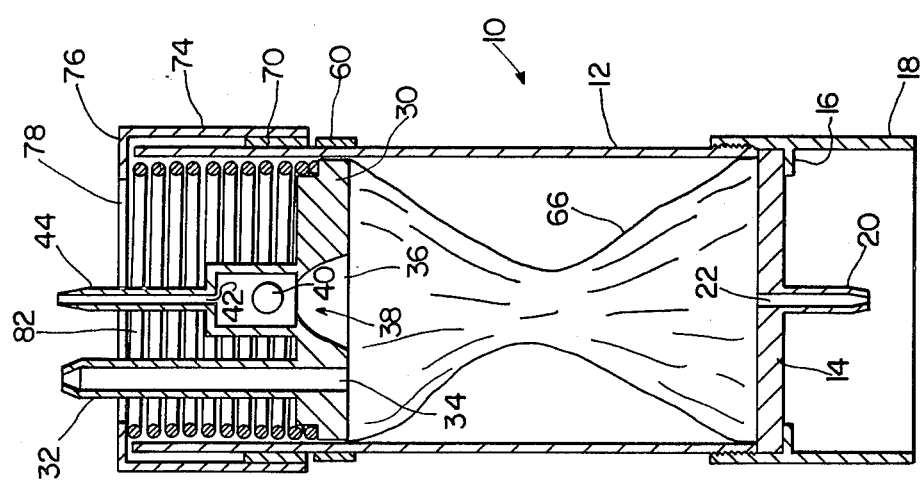
FIG. 1 is a cross-sectional elevation view of a disposable autotransfusion device according to the present.

With reference now to the drawings in which like numerals represent like elements throughout the several views, a presently preferred embodiment of the present invention is depicted in FIGS. 1 and 2 and comprises a disposable autotransfusion device 10 having a rigid cylindrical housing 12 which is preferably made of clear plastic. Located at the lower end of cylindrical housing 12 is a stationary wall 14. Stationary wall 14 is held against the bottom of cylindrical housing 12 by a flange 16 extending inwardly from a collar 18. As shown in FIG. 1, the top of collar 18 is threadably received on the bottom end of cylindrical housing 12 so that stationary wall 14 is positively held between the bottom end of cylindrical housing 12 and flange 16. A hose connection 20 containing an outlet 22 is integrally formed with stationary wall 14. As shown in FIG. 2, a return hose 24 is attached to hose connector 20. Return hose 24 has an adjustable clamp 26 attached thereto to prevent fluid flow through return hose 24 until desired.

Spaced above stationary wall 14 in cylindrical housing 12 is a movable wall 30. Integrally formed in movable wall 30 is a hose connector 32 having an inlet 34. Movable wall 30 is also provided with an outlet 36 which has the shape of an inverted cone portion. Located above outlet 36 is a float valve 38 having a float ball 40 and an outlet 42 which serves as a ball seat. Outlet 42 leads to a hose connector 44 as shown in FIG. 2. A suction hose 46 is attached to hose connector 44 and an aspirator hose 48 is connected to hose connector 32. Both suction hose 46 and aspirator hose 48 can be clamped by clamps 50 and 52, respectively.

As shown in FIG. 2, two lock portions 54 (only one of which is shown) are located on opposite sides on the periphery of movable wall 30. Lock portion 54 includes a vertical clearing channel 56 and a horizontal locking channel 58 in the peripheral side of movable wall 30. Surrounding movable wall 30 on the outside of cylindrical housing 12 is a locking sleeve 60. Locking sleeve 60 includes two lock pegs 62 (only one of which is shown) on opposite sides of the inner periphery of locking sleeve 60. Lock pegs 62 extend through cylindrical slots (not shown) in cylindrical housing 12 and into respective lock portions 54. When respective lock pegs 62 extend in respective locking channels 58, movable wall 30 is held stationary. However, when locking sleeve 60 is rotated to locate respective lock pegs 62 in respective clearing channels 56, movable wall 30 is free to move downwardly.

Disposed between movable wall 30 and stationary wall 14 is a blood bag 66. The side walls of blood bag 66 are shown in a collapsed position in FIG. 1, but it should be appreciated that blood bag 66 can extend to fill the entire space between the movable wall 30 and stationary wall 14. The upper end of blood bag 66 is attached around the periphery of movable wall 30 while the lower end of blood bag 66 is attached around the periphery of station wall 14. The blood bag 66 is so designed that when suction is applied to the bag so that the side walls tend to collapse the ratios of the cross section to length is such that the side walls cannot seal together as in an hour glass configuration.

Attached to the periphery of cylindrical housing 12 above locking sleeve 60 is a mounting sleeve 70. As shown in FIG. 2, mounting sleeve 70 has two J-channels 72 (only one of which is shown) on opposite sides thereof. A cylindrical cap 74 having a top flange 76 and a central aperture 78 extends about mounting sleeve 70 and the top of cylindrical housing 12. Cylindrical cap 74 also includes two mounting pegs 80 (only one of which is shown) which extend into respective ones of J-channels 72. Located between the top flange 76 of cylindrical cap 74 and the top of movable wall 30 is a compressed helical spring 82. In order to place helical spring 82 in cylindrical housing 12 under compression, cylindrical cap 74 is removed and helical spring 82 is located in cylindrical housing 12 on movable wall 30. Next, cylindrical cap 74 is placed on top of helical spring 82 and pushed downwardly so that mounting pegs 80 enter the long leg of J-channel 72 in mounting sleeve 70. Cylindrical cap 74 is then rotated and released so that mounting pegs 80 travel to the top of the small leg of J-channel 72. Because mounting pegs 80 are trapped in J-channel 72, cylindrical cap 74 is held to cylindrical housing 12 and helical spring 82 is maintained in compression.

In operation, disposable autotransfusion device 10 functions in the following manner. Initially, return hose 24 is clamped by clamp 26 and locking sleeve 60 is checked to make sure that movable wall 30 is securely locked in place with respective lock pegs 62 engaging locking channels 58. Next suction hose 46 is connected to hose connector 44 at one end and at the other end to a suitable source of negative pressure. It is specifically envisioned that a source of negative pressure suitable for these purposes is the negative pressure which is maintained in the collection chamber of an underwater drainage device such as the underwater drainage device disclosed in U.S. Pat. Nos. 3,363,626 and 3,363,627. Such an underwater drainage device will maintain a suction of approximately minus 20 centimeters of water which is a desirable level of negativity in order to prevent damage to formed elements of blood. An aspirator hose 48 is then attached to hose connector 32 at one end and to the pool of blood to be collected at the other end. Thus, due to the suction applied to the interior of blood bag 66, blood and air are drawn through aspirator hose 48 into the interior of blood bag 66. The blood drawn into blood bag 66 is deposited in blood bag 66 while the air is withdrawn through suction hose 46. It should be noted that the inverted cone-shaped of outlet 36 helps to prevent any liquid which may accumulate on the bottom of movable wall 30 from entering outlet 36 and being drawn into the suction source. The liquid which does accumulate on the bottom of movable wall 30 and which is drawn towards outlet 36 is not readily drawn up the incline walls of outlet 36.

As blood accumulates in blood bag 66, the collapsed side walls of blood bag 66 expand to fill the space between movable wall 30 and stationary wall 14. When blood bag 66 is filled to the desired level, aspirator hose 48 is removed from the suction source and clamped with clamp 52. At this time, another disposable autotransfusion device can be connected to the source of suction and to the patient to collect additional blood.

Before reintroducing the collected blood into the patient, it is essential to remove any air which may be contained in blood bag 66. In order to do this, locking sleeve 60 is rotated to move lock pegs 62 from respective locking channels 58 to respective clearing channels 56. This causes movable wall 30 to be pressed downward against the filled blood bag 66 by compressed spring 82. Compressed spring 82 exerts a pressure of approximately 100 to 300 mmHg. Next, clamp 50 is removed from suction hose 46 allowing air at the top of blood bag 66 to pass up outlet 36 and out of suction hose 46. However, when all of the air is gone from blood bag 66, the blood enters float valve 38 and raises float ball 40 into engagement with outlet 42. This prevents the blood in blood bag 66 from passing through suction hose 46. At this time, suction hose 46 is then clamped off with clamp 50 again.

In order to reintroduce the blood contained in blood bag 66 into the patient, return hose 24 is suitably connected to an appropriate filter and an I.V. tubing. With locking sleeve 60 already rotated so that movable wall 30 is released and being urged towards stationary wall 14 by compressed spring 82, adjustable clamp 26 is opened and used to regulate the blood flow from blood bag 66 through return hose 24 and back to the circulatory system of the patient. When all of the blood has been expelled from blood bag 66, return hose 24 is disconnected from the I.V. tubing and autotransfusion device 10 is discarded.

It should be appreciated that both the initial filling of blood bag 66 and the emptying of blood bag 66 is easily determined where cylindrical housing 12 is made of clear plastics. In addition, for convenience, disposable autotransfusion device 10 can be provided with hoses 24, 46 and 48 already attached to the respective hose connectors and with clamps 26, 50 and 52. In this manner, the entire device can be prepackaged in a sterilized container so as to be immediately ready for use when needed. The use of an underwater drainage device to provide the suction source for the present invention is also merely one example of a suitable suction source. However, it should be appreciated that the use of an underwater drainage device, such as that disclosed, provides the advantages associated with the use of the underwater drainage device with the additional advantage that a separate collection chamber is provided in which the blood can be collected and subsequently returned to the patient. The patient may be connected to the underwater drainage device in the conventional manner after the collection of blood for autotransfusion purposes.

Thus, while the invention has been described in detail with respect to an exemplary embodiment thereof, it will be understood by those of ordinary skill in the art that these and other variations and modifications may be effected in the exemplary embodiment within the scope and spirit of the invention.

What is claimed is:

1. An autotransfusion device for collecting blood from a pool in a patient and for subsequently returning the collected blood to the circulatory system of the patient comprising:
   a liquid collection chamber having a movable end wall, a stationary end wall and a flexible and collapsible side wall connecting said end walls;
   aspirator means for connecting said collection chamber to the pool in the patient;
   suction means including a port into said collection chamber for connecting the collection chamber to a source of negative pressure;
   discharging means for resiliently urging said movable wall towards said stationary wall; and
   locking means for releasably locking said movable wall spaced from said statinary wall while the liquid chamber is being filled; and
   return means for connecting the collection chamber to the circulatory system of the patient such that said suction means draws blood from the pool through said aspiratory means until said collection chamber is adequately filled and subsequently said discharging means is released to force the collected blood back to the circulatory system through said return means.

2. An autotransfusion device as claimed in claim 1 wherein said aspirator means and said suction means are connected at the top of said collection chamber and said return means is connected at the bottom of said collection chamber.

3. An autotransfusion device as claimed in claim 2 wherein said suction means includes an inverted cone-shaped outlet from said collection chamber which acts to prevent liquids from being drawn into said suction means and to facilitate the removal of any gas within the collection chamber.

4. An autotransfusion device as claimed in claim 1 wherein said suction means includes a float valve to prevent liquids from entering said suction means when said collection chamber is filled.

5. An autotransfusion device as claimed in claim 1 wherein said discharging means is a spring which presses against said movable wall.

6. An autotransfusion device for collecting blood from a pool in a patient and for subsequently returning the collected blood to the circulatory system of the patient comprising:
   a rigid cylindrical housing having a bottom wall, a movable piston wall, and a collection chamber located between said bottom wall and said piston wall;
   an aspirator inlet located in said piston wall which is connected by a hose to the pool in the patient;
   a suction outlet also located in said piston wall which is connected by a hose to a source of negative pressure;
   a liquid outlet located in said bottom wall which is connected by a hose to the circulatory system of the patient;
   clamping means for selectively clamping said hoses attached to said aspirator inlet, said suction outlet, and said liquid outlet;
   means located in said cylindrical housing for resiliently urging said piston wall towards said bottom wall;
   and
   locking means for releasably locking said piston wall spaced from said bottom wall during collection of the blood such that after said collection chamber is adquately filled, said locking means is released to force the blood collected from said collection chamber to the circulatory system of the pateint as said piston wall is urged towards said bottom wall.

7. An autotransfusion device as claimed in claim 6 wherein a blood bag having flexible side walls is attached to the peripheries of said bottom wall and said piston wall to form said collection chamber in said cylindrical body.

8. An autotransfusion device as claimed in claim 6 wherein said locking means includes a sleeve which is rotatably mounted about said cylindrical body and which engages said piston wall, said sleeve including a means for releasing said piston wall from engagement as said sleeve is rotated.

9. An autotransfusion device as claimed in claim 6 wherein the bottom of said suction outlet includes an inverted cone-shaped portion and a float valve is located above said cone-shaped portion.

10. An autotransfusion device as claimed in claim 6 wherein said urging means is a helical spring located within said cylindrical body and which is compressed against the top of said piston wall.

11. An autotransfusion device as claimed in claim 6 wherein said clamping means for said liquid outlet is an adjustable clamp which controls the flow of liquid from collection chamber.

* * * * *